(12) United States Patent
Tidwell (10) Patent No.: US 10,159,823 B2
(45) Date of Patent: Dec. 25, 2018

(54) TOPICAL SUBSTANCE APPLICATION DEVICE INCLUDING APPLICATOR

(71) Applicant: C. R. Bard, Inc., Murray Hill, NJ (US)

(72) Inventor: Jeremy A. Tidwell, Lehi, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 339 days.

(21) Appl. No.: 15/192,710

(22) Filed: Jun. 24, 2016

(65) Prior Publication Data

US 2016/0375233 A1    Dec. 29, 2016

Related U.S. Application Data (60) Provisional application No. 62/185,434, filed on Jun. 26, 2015.

(51) Int. Cl.
*A61M 35/00* (2006.01)
*A61F 13/40* (2006.01)

(52) U.S. Cl.
CPC ........ *A61M 35/003* (2013.01); *A61M 35/006* (2013.01)

(58) Field of Classification Search
CPC .......................... A61M 35/003; A61M 35/006
See application file for complete search history.

(56) References Cited

U.S. PATENT DOCUMENTS

| | | |
|---|---|---|
| 3,204,278 A | 9/1965 | Lambros |
| 3,207,299 A | 9/1965 | Sparks |
| 3,315,801 A | 4/1967 | Lowry |
| 3,438,550 A | 4/1969 | Young |
| 3,521,805 A | 7/1970 | Ward |
| 3,577,258 A | 5/1971 | Sincavage et al. |
| 3,917,116 A | 11/1975 | Mason |
| 3,986,640 A | 10/1976 | Redmond |
| 4,127,339 A * | 11/1978 | Malacheski ......... A61M 35/003 222/92 |

(Continued)

FOREIGN PATENT DOCUMENTS

| | | |
|---|---|---|
| WO | 2008/113973 A1 | 9/2008 |
| WO | 2016/210342 A1 | 12/2016 |

OTHER PUBLICATIONS

PCT/US2016/039385 filed Jun. 24, 2016 International Search Report and Written Opinion dated Sep. 13, 2016.

*Primary Examiner* — Tatyana Zalukaeva
*Assistant Examiner* — Gabriella Burnette
(74) *Attorney, Agent, or Firm* — Rutan & Tucker, LLP (57) ABSTRACT

An application device for dispensing a fluid, including a liquid, gel, topical fluid, or other flowable substance, stored within a volume of the application device package is disclosed. The application device is manually deformable so as to permit breakage and establish an opening to the volume storing the topical fluid. In one embodiment, the application device comprises a sealed package that defines a volume in which the fluid is disposed. The package includes a partial slit that is configured to provide an opening to the volume when the package is deformed. The opening is configured to enable the fluid to be released from the volume. An applicator element is also included within the package and exposed upon package opening. The applicator element can include a gauze, foam, compliant pad, or other suitable element, and is configured to assist with dispersion of the fluid on a surface, such a patient's skin.

18 Claims, 12 Drawing Sheets

(56) References Cited

U.S. PATENT DOCUMENTS

| | | |
|---|---|---|
| 4,140,409 A | 2/1979 | DeVries |
| 4,236,652 A | 12/1980 | Beguhn |
| 4,430,013 A | 2/1984 | Kaufman |
| 4,493,574 A | 1/1985 | Redmond et al. |
| 4,611,715 A | 9/1986 | Redmond |
| 4,658,963 A | 4/1987 | Jud |
| 4,812,067 A | 3/1989 | Brown et al. |
| 4,963,045 A | 10/1990 | Willcox |
| RE34,087 E | 10/1992 | Redmond |
| 5,263,609 A | 11/1993 | Hoshino |
| 5,380,110 A | 1/1995 | Festa |
| 5,490,736 A | 2/1996 | Haber et al. |
| 5,494,192 A | 2/1996 | Redmond |
| 5,640,737 A | 6/1997 | Boggs |
| 5,741,564 A | 4/1998 | Gillberg-LaForce |
| 6,041,930 A | 3/2000 | Cockburn |
| 6,371,675 B1 | 4/2002 | Hoang et al. |
| 6,403,033 B1 | 6/2002 | Gutman |
| 6,488,428 B1 | 12/2002 | Fischer |
| 6,823,994 B2 | 11/2004 | Tsaur |
| 6,945,391 B2 | 9/2005 | Moodie |
| 7,004,354 B2 | 2/2006 | Harper |
| 7,121,409 B1 | 10/2006 | Hamilton et al. |
| 7,163,101 B2 | 1/2007 | Harper |
| 7,179,007 B2 | 2/2007 | Wong et al. |
| 7,285,114 B2 | 10/2007 | Harper |
| 7,419,321 B2 | 9/2008 | Tereschouk |
| 7,506,762 B2 | 3/2009 | Nelson et al. |
| 7,552,823 B2 * | 6/2009 | Schuehrer ............ A45D 34/04 206/469 |
| 7,757,893 B2 | 7/2010 | Perell |
| 7,987,985 B2 | 8/2011 | Ede et al. |
| 8,069,985 B2 | 12/2011 | Burattini |
| 8,104,986 B2 | 1/2012 | Nash |
| 8,157,464 B2 | 4/2012 | Prax |
| 8,225,932 B2 | 7/2012 | Burattini |
| 8,651,761 B2 | 2/2014 | Maloney et al. |
| 8,662,349 B2 | 3/2014 | Genosar et al. |
| 8,910,817 B2 | 12/2014 | Kanderka et al. |
| 8,919,594 B2 | 12/2014 | Teys |
| 2005/0263431 A1 | 12/2005 | Mahon et al. |
| 2005/0269219 A1 * | 12/2005 | Discko, Jr. .......... A61M 35/003 206/219 |
| 2006/0112967 A1 | 6/2006 | Fleming |
| 2006/0115520 A1 | 6/2006 | Vanek et al. |
| 2009/0241277 A1 | 10/2009 | Lam et al. |
| 2010/0198166 A1 | 8/2010 | Callahan et al. |
| 2010/0264044 A1 | 10/2010 | Beihoffer et al. |
| 2013/0121749 A1 * | 5/2013 | Maloney ................ A47L 13/17 401/133 |
| 2014/0231296 A1 | 8/2014 | Reggio et al. |
| 2014/0353336 A1 | 12/2014 | Zaporski et al. |
| 2015/0083750 A1 | 3/2015 | Sutherland |
| 2015/0136639 A1 | 5/2015 | Aranda Lopez |

* cited by examiner

TOPICAL SUBSTANCE APPLICATION DEVICE INCLUDING APPLICATOR

CROSS-REFERENCE TO RELATED APPLICATIONS

This application claims the benefit of U.S. Provisional Patent Application No. 62/185,434, filed Jun. 26, 2015, and titled "TOPICAL SUBSTANCE APPLICATION DEVICE INCLUDING APPLICATOR," which is incorporated herein by reference in its entirety.

BRIEF SUMMARY

Briefly summarized, embodiments of the present invention are directed to an application device for dispensing a fluid, including a liquid, gel, topical fluid, or other flowable substance, stored within a volume of the application device package is disclosed. The application device is manually deformable so as to permit breakage and establish an opening to the volume storing the topical fluid.

In one embodiment, the application device comprises a sealed package that defines a volume in which the fluid is disposed. The package includes a partial slit that is configured to provide an opening to the volume when the package is deformed. The opening is configured to enable the fluid to be released from the volume. An applicator element is also included with the package. The applicator element can include a gauze, foam, compliant pad, or other suitable element, and is configured to assist with dispersion of the fluid on a surface, such a patient's skin.

The applicator element can be included within the volume and exposed upon opening of the package, can be attached to an exterior portion of the package, or can be otherwise included with the application device. It is appreciated that the application device described herein can be employed in a variety of environments, circumstances, and applications, both medical and non-medical, as may be appreciated.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an application device for dispensing a fluid, including a liquid, gel, a topical substance, or other flowable substance, stored within a volume of the application device package. The application device is manually deformable so as to permit breakage along a partial slit or perforation to establish an opening to the volume storing the topical fluid. An applicator element is attached to or otherwise included with the application device package and is configured to assist with dispersion of the fluid, such as on the skin of the patient in the case of an ultrasound gel, antimicrobial cleansing solution, or other topical fluid, for instance. The applicator can include a gauze, a cushion tip, a compliant pad, or other suitable structure. The applicator can be included within the volume and exposed upon opening of the package, can be attached to an exterior portion of the package, or can be otherwise included with the application device. It is appreciated that the application device described herein can be employed in a variety of environments, circumstances, and applications, both medical and non-medical, as may be appreciated.

Figure 1A:
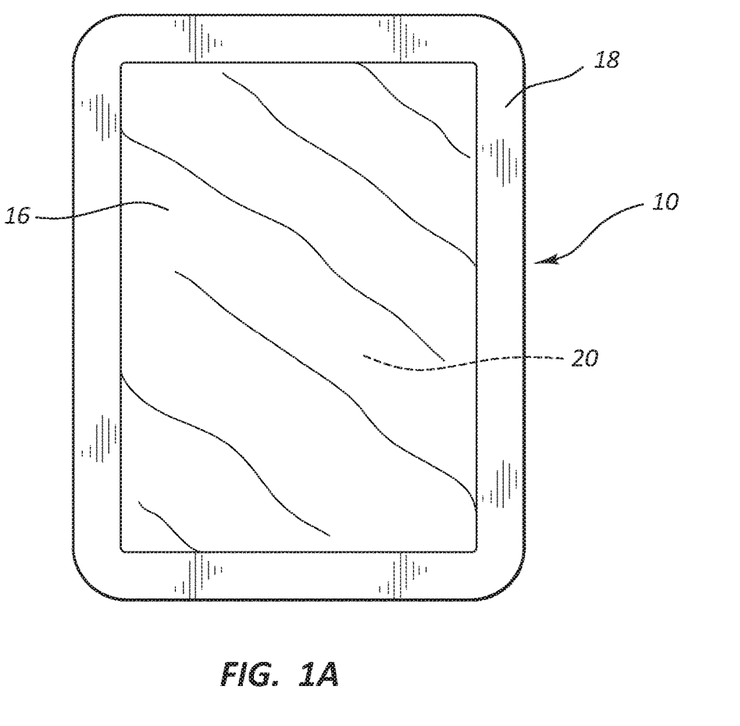
FIGS. 1A and 1B depict various views of an application device in accordance with one embodiment.
Figure 1B:
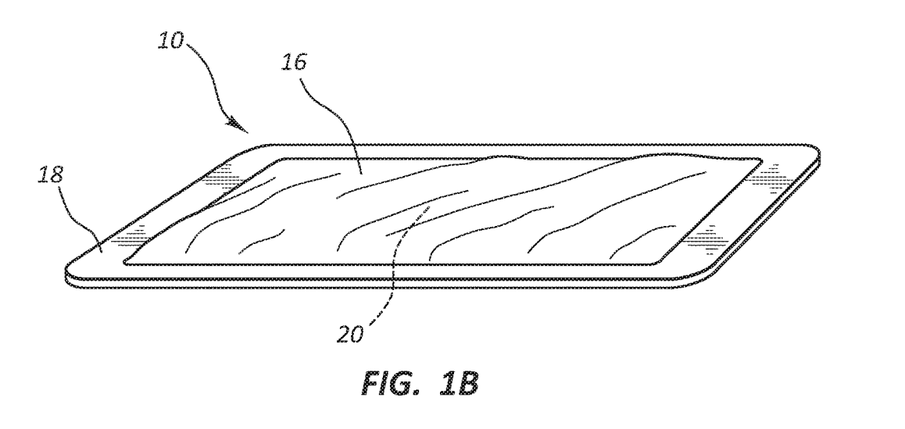
Figure 2:
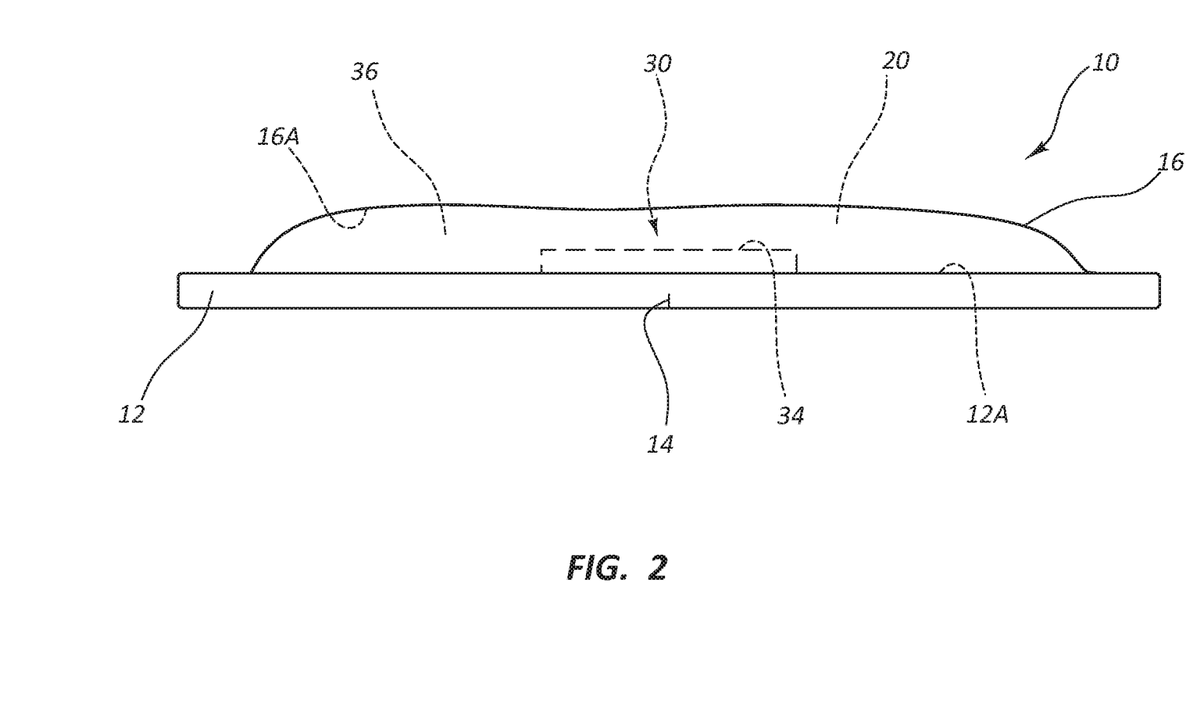
FIG. 2 is a cross-sectional side view of the application device of FIG. 1.

FIGS. 1A-2 depict various features of an application device ("device"), generally designated at 10, according to one embodiment. As shown, the device 10 includes a package that includes a semi-rigid, flat base sheet 12 including polystyrene or other suitable material. The base sheet 12 includes a perforation or partial slit 14 that extends across a mid-line width of the base sheet. The partial slit 14 is defined through only a portion of the thickness of the base sheet 12 so as to leave the base sheet initially unbreached. Note that the location, length, etc., of the partial slit can vary from what is shown and described herein. In one embodiment, the base sheet 12 includes polypropylene, though other sheet materials are also possible.

A cover sheet 16 including a thermoplastic and/or metallic foil or other suitable material is disposed over the base sheet 12 and is sealed to the base sheet via heat sealing or other suitable process to define a sealed perimeter 18 along an outer perimeter of the device 10. As a result of the sealed perimeter 18, a volume 20 is defined between the base sheet 12 and the cover sheet 16. The size of the volume 20 can be modified according to need, design, desire, etc., during manufacture. So configured the device 10 forms a rectangular sealed package capable of holding and dispensing a fluid, as shown and discussed below. It is appreciated that the package can define other shapes, including square, round, triangular, hourglass-shaped, semicircular, oval, and other geometric or other shapes. Also, the shape defined by the perimeter 18 can also vary from the rectangular shape shown and described herein. Note also that the size of the device 10 can also vary. For instance, in the present embodiment, the device outer perimeter measures about 1.5 inches by about 2 inches, but other smaller and larger sizes are possible. In one non-limiting embodiment, for instance, the device dimensions can range from about 40 mm×50 mm to about 85 mm×100 mm. Other sizes are also possible.

The device 10 includes a fluid 36 that is contained within the volume 20 until the device is breached, which enables the fluid to escape the volume and be dispensed for use. The fluid 36 can include any fluid that is employed during medical procedures, for instance, or for other purposes. In one embodiment, the fluid 36 is a topical fluid for use on the skin of a patient, such as for disinfecting the skin surface or providing lubrication. Examples of such topical fluids includes CHG, CHA, IPA, saline, ethyl alcohol and other alcohols, ultrasound gel and other gels, skin prep solution, iodine, tincture of benzoin, licocaine, lotions, ointments, creams, flowable substances, etc. Many other medical and non-medical fluids/substances can be included in the volume 20.

In the present embodiment, the device 10 further includes an applicator element ("applicator") 30 that is permanently or removably attached to the device 10. In the embodiment shown in FIG. 2, for instance, the applicator 30 includes a piece of gauze 34 that is secured to an inner surface 12A of the base sheet 12 proximate the partial slit 14. As will be seen below, the applicator 30 is used to help distribute and disperse the fluid 36 after exiting the volume 20. It is appreciated that various other components can be employed as the applicator, as is seen further below, and other mounting locations for the applicator are also possible.

Figure 3:
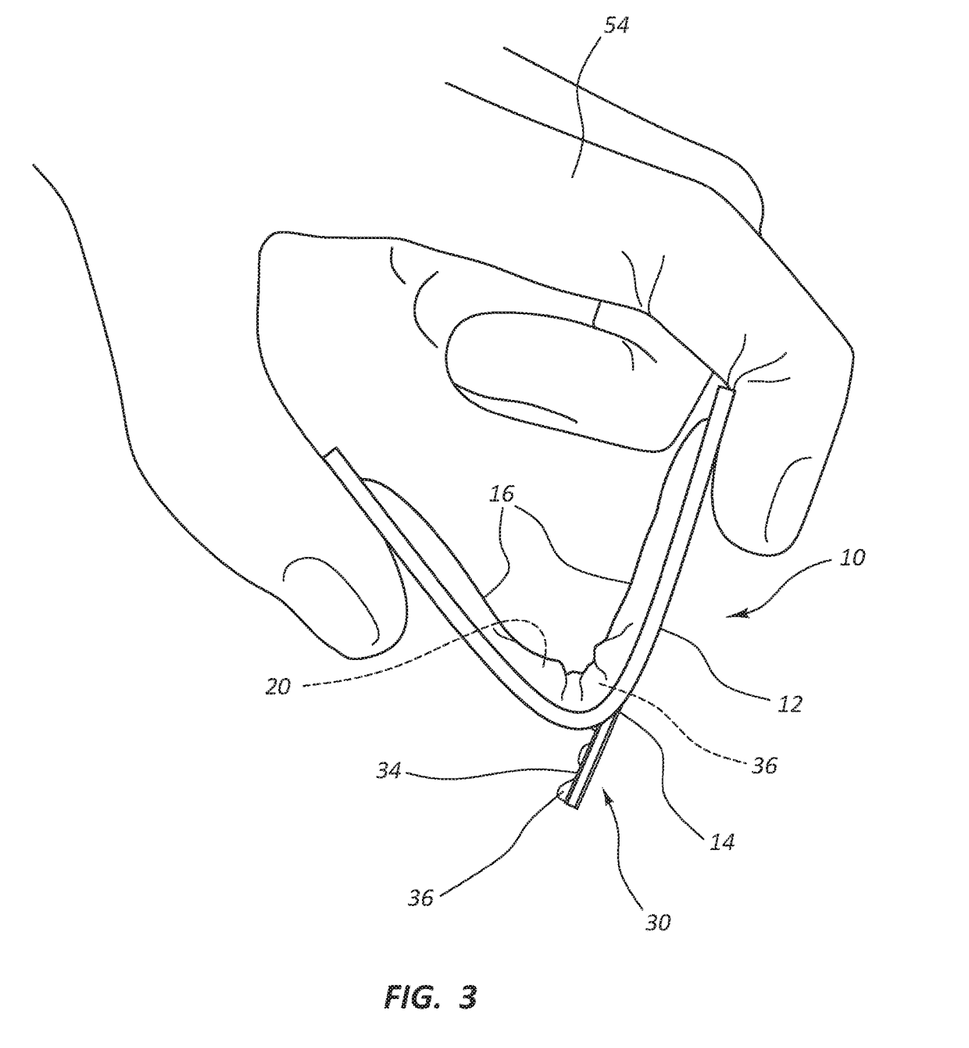
FIG. 3 shows the application device of FIG. 1 in use.

FIG. 3 depicts a user opening the device 10 to eject and disperse the fluid 36 for use. As shown, either longitudinal end of the device 10 is manually grasped by a hand 54 of a user and pressed so as to deform the device with the base sheet 12 extending outwardly. This causes at least a portion of the break line defined by the partial slit 14 to rupture and become unsealed, creating an opening 38 (FIG. 4) along the partial slit. The opening 38 enables the fluid 36 to flow from the volume 20. As shown in FIG. 3, the applicator 30 is positioned at the opening 38 so that the fluid 36 flowing from the opening 38 is incident on and/or proximate to the applicator, in this case the gauze 34. The user, while still grasping the opened device 10, can use the applicator 30—which as mentioned before is mounted to the inner surface 16A of the base sheet 16 in the present embodiment—to disperse the fluid 36 on the skin of the patient or other surface and distribute the fluid as needed. Once the fluid 36 has been expelled from the volume 20 and distributed as needed, the device 10 with the included applicator 22 can be discarded. Note that the device 10 is configured so it can be used with a single hand. Note also that the device 10 enables dispersion of the fluid without the hand or fingers of the user needing to touch the fluid.

In the present embodiment, the gauze 34 is permanently attached to the device 10 so that it remains therewith. Such attachment can be achieved via the use of a suitable adhesive, heat staking, etc., to the inner surface 16A of the base sheet 16, an inner surface 12A of the cover sheet 12, or other suitable attachment location. In another embodiment, the applicator 30 can be removably attached to the device 10 such as by a mechanical/friction fit. In this way, the gauze 34/other applicator 30 remains in place during use, but can also be manually removed by the user should separate use of the applicator be desired. Note also that the size, shape, type, etc., of the applicator can vary from what is shown and described herein.

Figure 4:
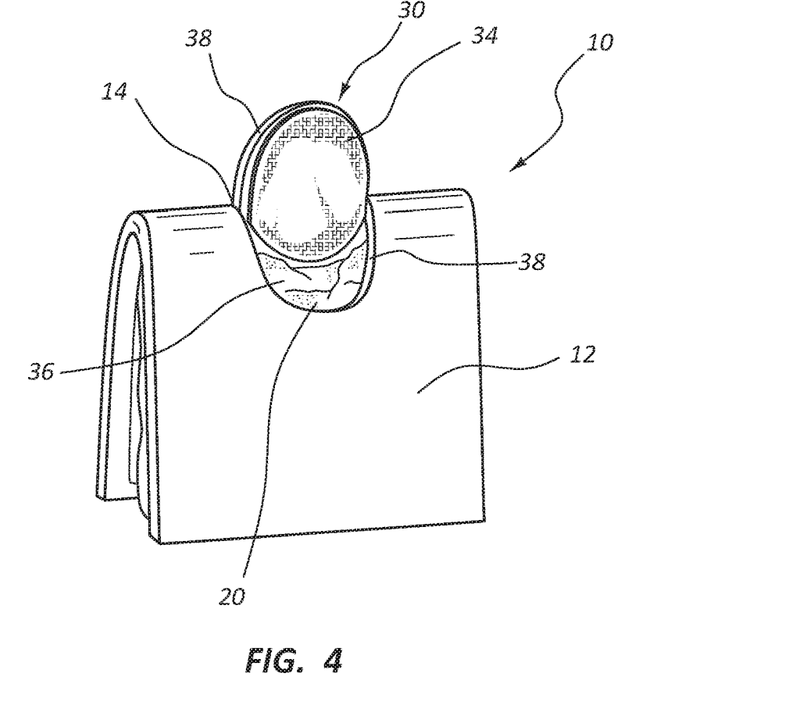
FIG. 4 is an end view of the application device of FIG. 1 after opening.

FIG. 4 shows that, in one embodiment, the shape of the opening 38 can vary, including rounded (as in FIG. 4), semicircular, linear, oval, triangular, etc. Also, note that the partial slit 14 does not span the entire width of the base sheet 12, but rather only a central portion thereof.

Figure 5:
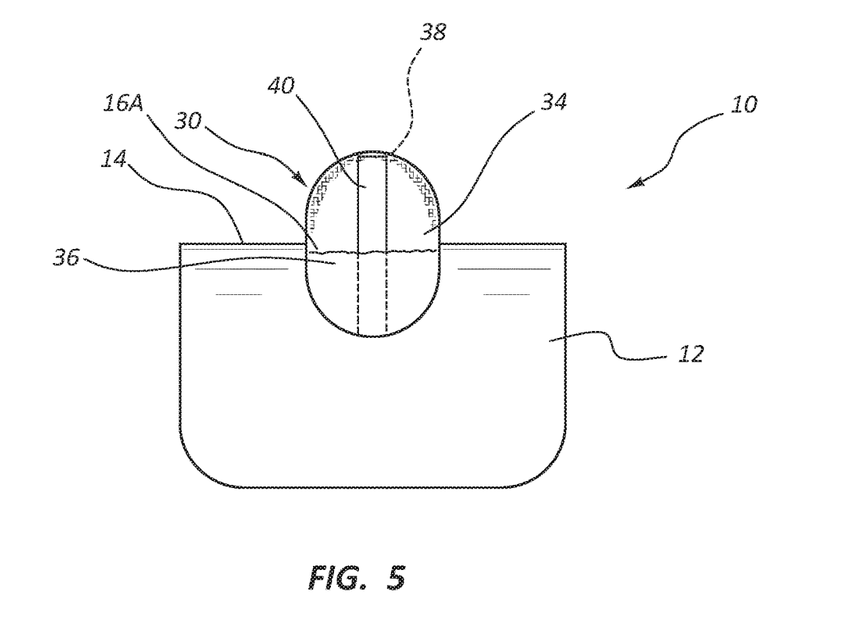
FIG. 5 is an end view of an application device according to one embodiment.

In the embodiment shown in FIG. 5, the applicator 30 includes the gauze 34 located proximate the opening 38 exposed after breaking of the partial slit 14 to define the opening 38. FIG. 5 further shows that, in one embodiment, a reinforcement element 40, such as a piece of wire, can be included beneath the gauze 34 or other applicator so as to assist in rupture of the break line of the partial slit 14 and consequent full deployment of the opening 38. This helps also to maintain the patency of the opening 38 during use of the device 10. The reinforcement element 40 can be secured to the inner surface 16A of the base sheet 12, or other suitable surface. In another embodiment, more than one gauze can be included in the volume 20 and exposed upon establishment of the opening 38 so as to increase fluid dispersal surfaces.

As mentioned, the applicator can include one or more of a variety of elements, including a gauze, woven and nonwoven material, a Q-tip-like cushion tip, cotton pads, polymeric pads and materials, sponge materials, closed-cell and open-cell foams, etc. The applicator can be absorbable or non-absorbable.

Figure 6:
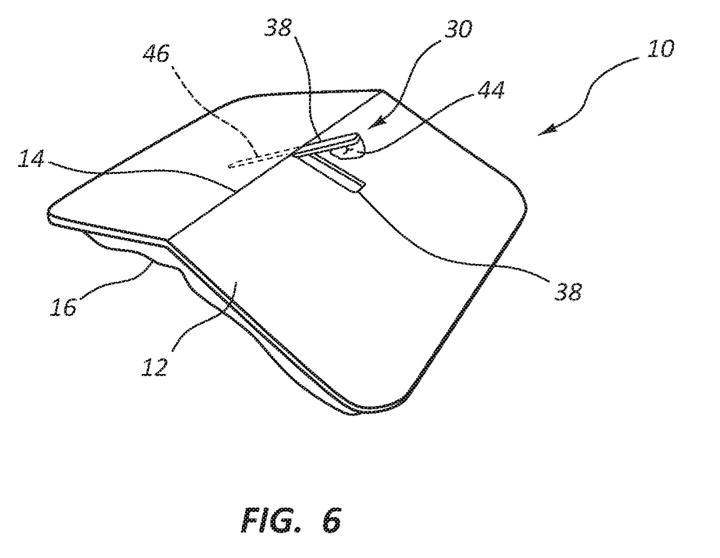
FIG. 6 is a perspective view of an application device according to one embodiment.
Figure 7:
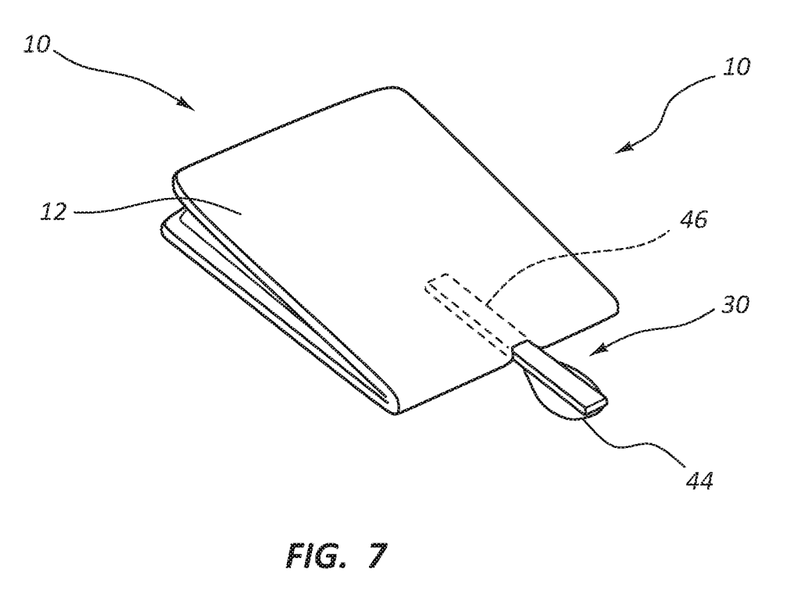
FIG. 7 shows the application device of FIG. 6 in use.

FIGS. 6 and 7 give another example of the applicator element 30 according to one embodiment, wherein the applicator includes a Q-tip-shaped applicator pad 44 that is initially disposed within the volume 20 of the device 10 until the partial slit 14 is breached to define the opening 38. Once the opening 38 is defined, the applicator pad 44 can extend from the opening and be used to disperse the fluid 36. The applicator pad 44 is attached to a rod 46, which is secured to the inner surface 12A of the base sheet 12 in the present embodiment, and which acts as a reinforcement element, such as the reinforcement element 40 shown in FIG. 5. Note that the partial slit 14, and the opening 38 created when the partial slit is breached during deformation of the application device package, can define other than linear shapes, such as the composite shape of the partial slit in FIGS. 6 and 7, so as to provide a suitable opening for exposure of the applicator element 30. Thus, these and other non-linear partial slit/opening shape configurations are contemplated.

Figure 8:
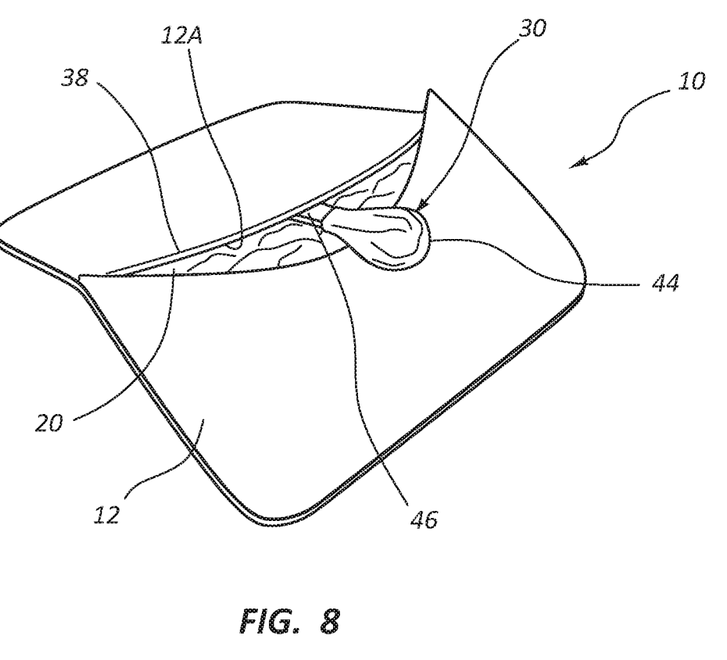
FIG. 8 is a perspective view of an application device according to one embodiment.

FIG. 8 shows a variation of the configuration depicted in FIGS. 6 and 7, wherein the opening 38 is relatively larger and defines an arc or semi-circular shape. These and other modifications are therefore contemplated.

Figure 9:
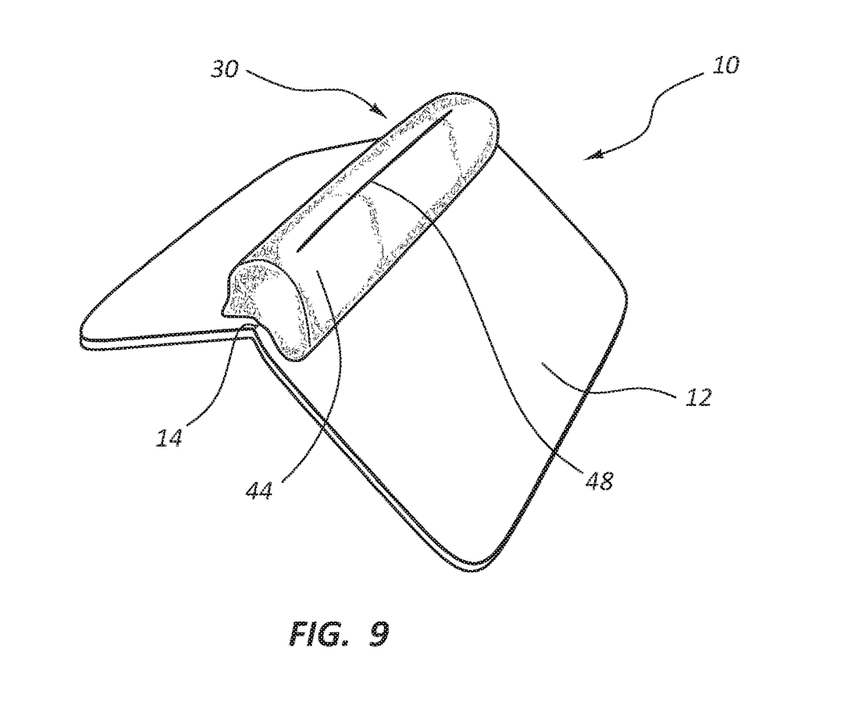
FIG. 9 is a perspective view of an application device according to one embodiment.
Figure 10:
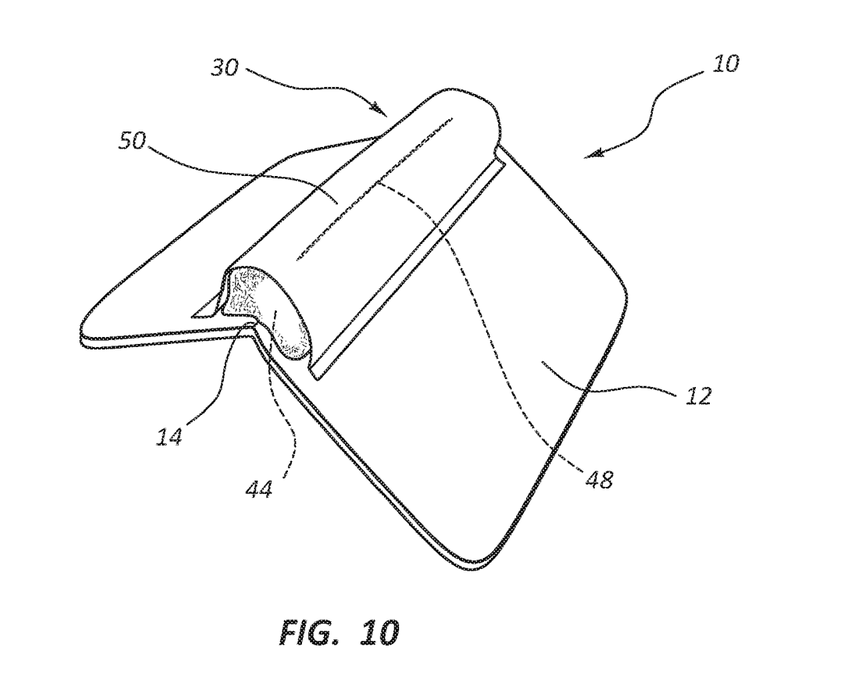
FIG. 10 is a perspective view of an application device according to one embodiment.

FIG. 9 depicts details of the applicator element 30 according to another embodiment, wherein the applicator pad 44 spans the width of the device 10 and is attached to the outer surface thereof. As shown, the applicator pad 44 is attached (via adhesive or other suitable mode) so as to be disposed atop the partial slit 14 and subsequent opening 38. An incision 48 is defined through the applicator pad 44 to enable the fluid 36 to pass from the opening 38 and rise to the surface of the applicator pad, where it may be dispersed by the user, as desired. The applicator pad 44 in the present embodiment includes a compliant foam material, though other materials can also be employed. In FIG. 10, a containment element, such as a covering 50, is placed atop the applicator pad 44 to shield the incision 48 and help contain and control emission of the fluid from the incision. The covering 50 in one embodiment includes a cotton or synthetic gauze material, though other materials can also be used.

Figure 11:
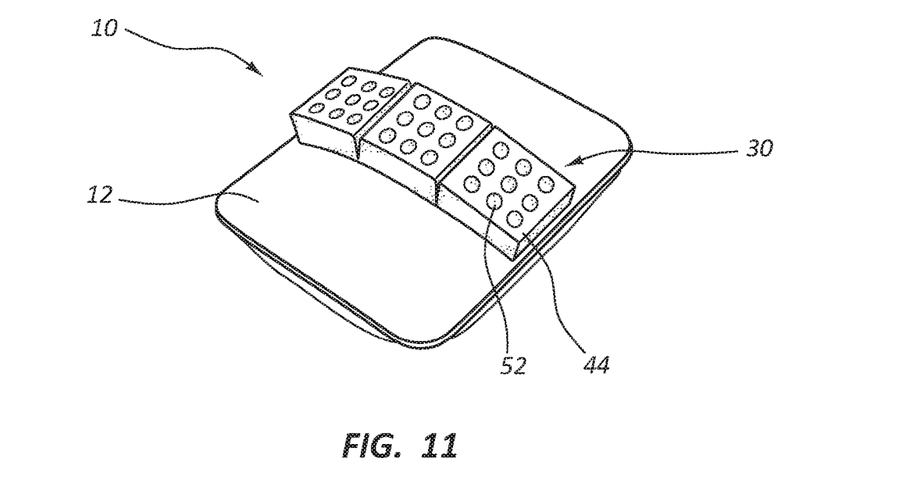
FIG. 11 is a perspective view of an application device according to one embodiment.

FIG. 11 depicts details of the applicator element 30 according to another embodiment, wherein the applicator pad 44 spans the width of the device 10 and is attached to the outer surface thereof. As shown, the applicator pad 44 is attached (via adhesive or other suitable mode) so as to be disposed atop the partial slit 14 and subsequent opening 38. A plurality of holes 52 are defined through the applicator pad 44 to enable the fluid 36 to pass from the opening 38 and rise to the surface of the applicator pad, where it may be dispersed by the user, as desired. As such, the holes 52 are one example of one or more apertures that can be defined in the applicator element to enable fluid to migrate to a top surface of the applicator element. Other examples of apertures are contemplated.

The applicator pad 44 in the present embodiment includes a compliant foam material, though other materials can also be employed. Note that the holes 52 in the present embodiment are round and cylindrically shaped, though they may take other forms and configurations in other embodiments.

Figure 12:
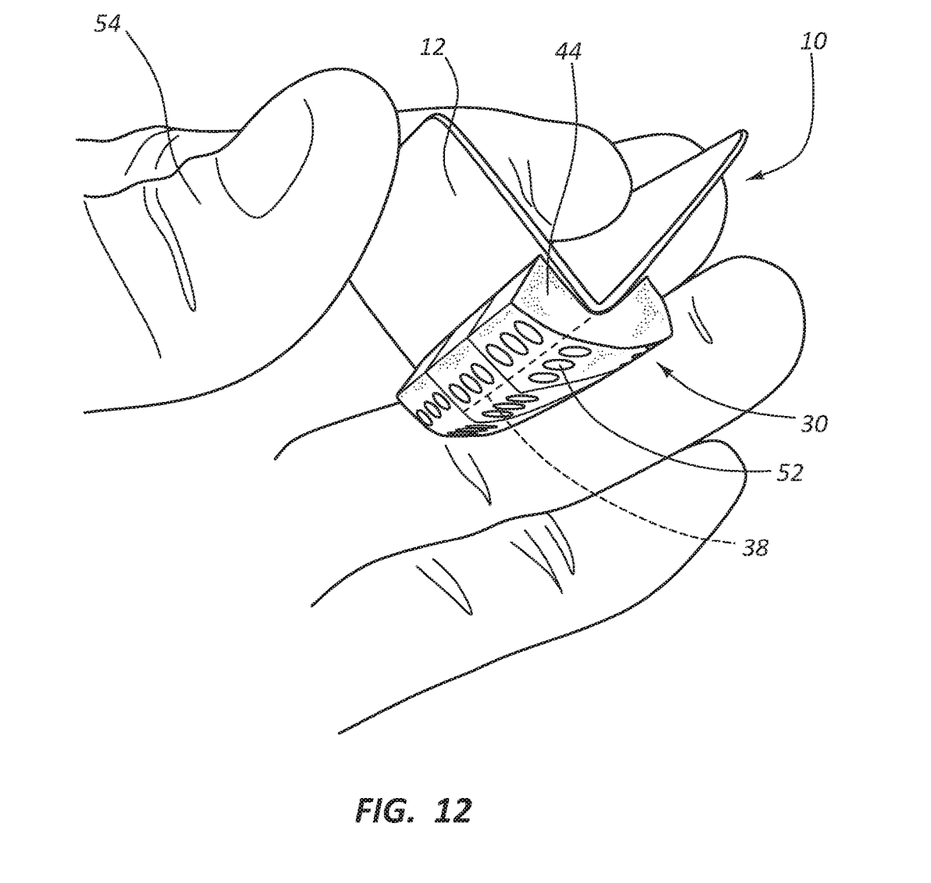
FIG. 12 shows the application device of FIG. 11 in use.

FIG. 12 shows the hand 54 of a user grasping and deforming the device 10 so as to break the partial slit 14 open and enable the fluid 36 to escape from the resultant opening 38. As described, by virtue of the applicator pad holes 52 the fluid 36 exiting the opening 38 can travel to the exterior surface of the applicator pad 44, where it can be dispersed by movement by the user of the applicator pad over the patient's skin or other surface.

Figure 13:
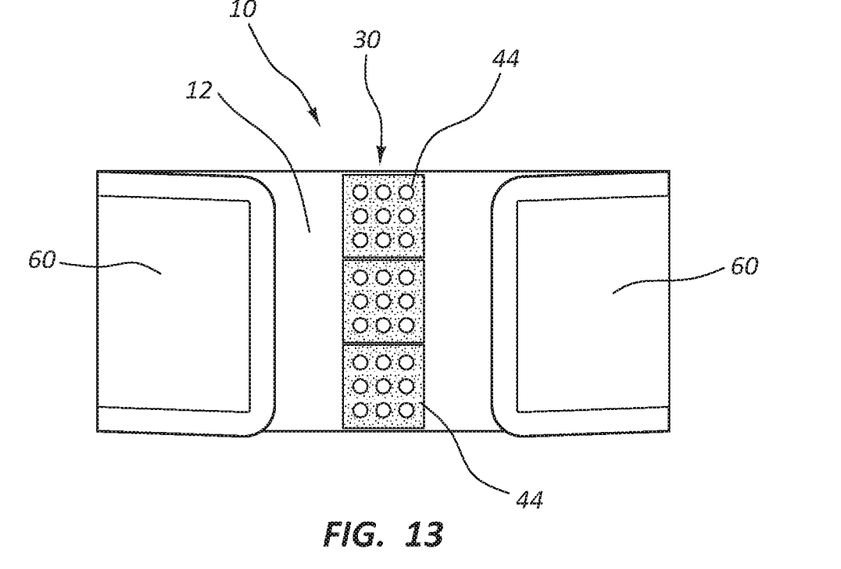
FIG. 13 is a bottom view of an application device according to one embodiment.
Figure 14:
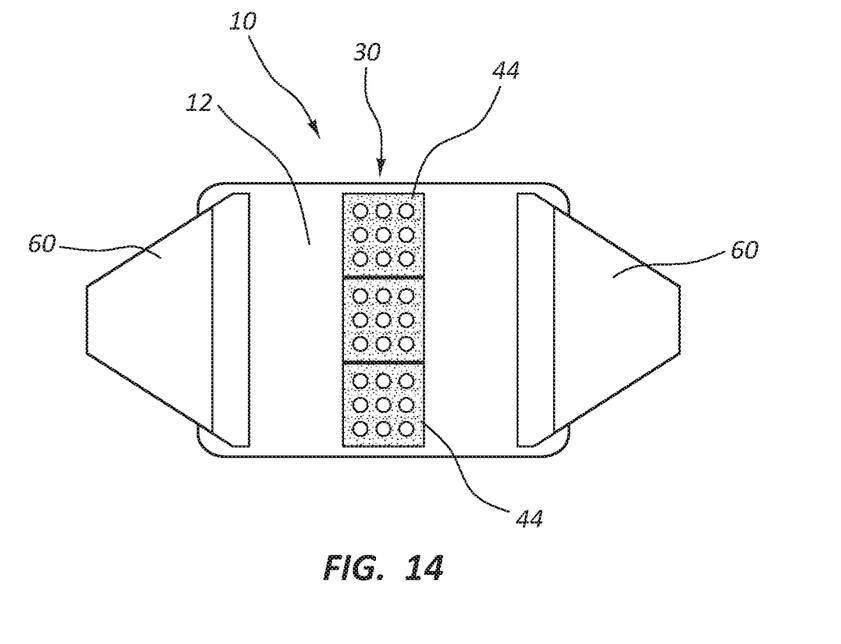
FIG. 14 is a bottom view of an application device according to one embodiment.
Figure 15A:
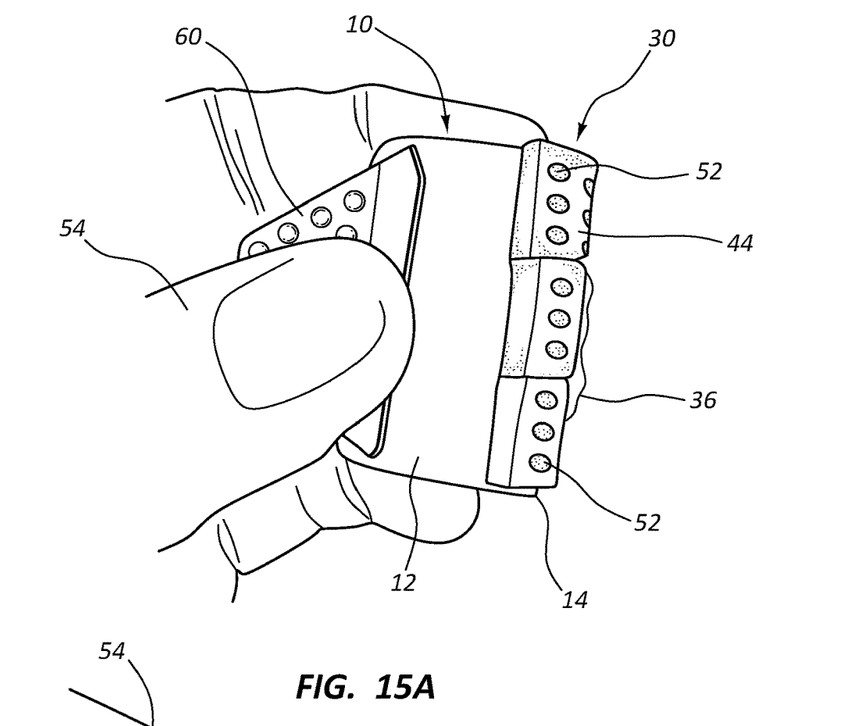
FIGS. 15A and 15B depict use of the application device of FIG. 14.
Figure 15B:
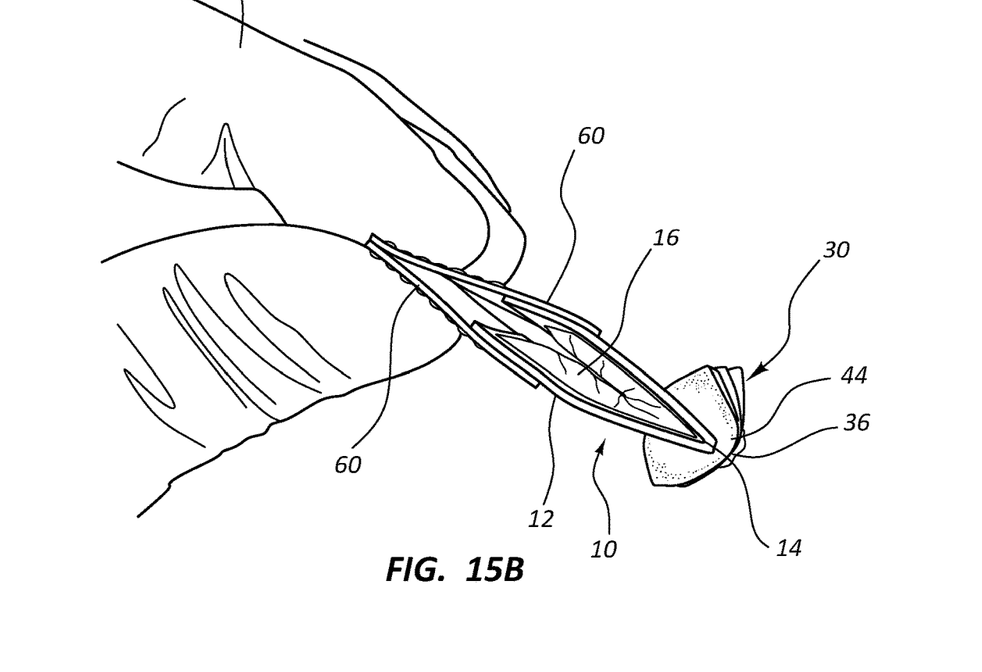

FIGS. 13 and 14 depict details of the device 10 according to another embodiment, wherein the device includes finger tabs 60 that extend from either longitudinal end of the device to assist with grasping and squeezing of the device during use, as shown in FIGS. 15A and 15B. In particular, FIG. 13 shows rectangular tabs 60 added to the device 10, while FIG. 14 shows truncated triangular-shaped tabs. As such, it is appreciated that the size, shape, positioning, and other configurations of the tabs can vary from what is shown and described herein.

In one embodiment, gripping material and/or surfaces features can be added to the exterior of the device 10 and/or the tabs 60 to more easily enable grasping of the device by the user. Such features include surface roughness or roughening material applied to the device exterior/tabs 60, including textures, ridges, rubberized surfaces, dimples, etc.

In one embodiment, the color of the exterior of the device 10 can be chosen so as to identify the purpose of the device or the composition/purpose of the fluid 36 therein. Also, note that, though one use of the fluid is as a "topical fluid," the fluid 36 contained by the device 10 can be employed for a variety of uses, both topical and non-topical. Examples of use of the topical fluid include skin prep and disinfecting, skin treatment and rehabilitation, skin numbing, medicament application, medical device cleaning, etc.

Figure 16:
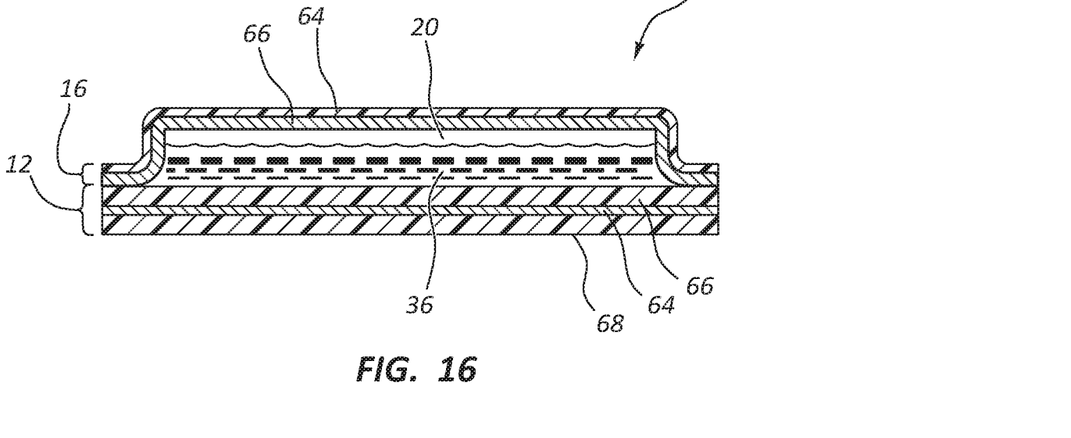
FIG. 16 is a partially exploded edge-on view of an application device according to one embodiment.

FIG. 16 shows a partially exploded view of the device 10 according to one embodiment, wherein the base sheet 12 includes a thermoplastic backer layer 68 on which a metallic foil layer 64 is disposed, with a polypropylene layer 66 atop the foil layer. Correspondingly, the cover sheet 16 includes a polypropylene layer 66 on which a metallic foil layer 64 is disposed. The various layers for the base sheet 12 and cover sheet 16 can be laminated together before being used to form the device 10, or can be mated together at the time of forming the device. Formation of the package of the device 10 with the aforementioned layers 64, 66, and 68 enables the finished device 10 to withstand ethylene oxide-based sterilization procedures without causing degradation/alteration of the fluid 36 disposed within the volume 20. In particular, the metallic foil layers 64 prevent the ethylene oxide gas from permeating the device package, thus preserving the integrity of the volume contents. It is appreciated that the order and number of layers can vary from what is shown and described in connection with FIG. 16.

In one embodiment, it is appreciated that the device 10 can be manufactured by a process including the placement of a quantity of the liquid between the base sheet 12 and the cover sheet 16 before sealing the base sheet to the cover sheet to define the perimeter 18 and encapsulating the liquid 36 within the volume 20 bounded by the perimeter. In one embodiment, a heat sealing process is used to define the perimeter 18. The partial slit 14 can be defined on the base sheet 12 either before or after sealing.

If it is to be disposed within the volume 20, the applicator element 30 or reinforcement element 40 is placed/secured within the volume before sealing, such as via adhering the applicator element or reinforcement element to the inner surface 12A of the base sheet 12. If the applicator element 30 is to be disposed on an exterior portion of the device 10, the applicator element is affixed to the device exterior portion, such as via and adhesive, after sealing of the device is complete. In addition to these, other process stages can be employed. In one embodiment, the base sheet can be sealed on three sides to the cover sheet before the volume therebetween is expanded by a puff of air, after which the fluid is injected into the volume. The fourth side can then be sealed.

Figure 17:
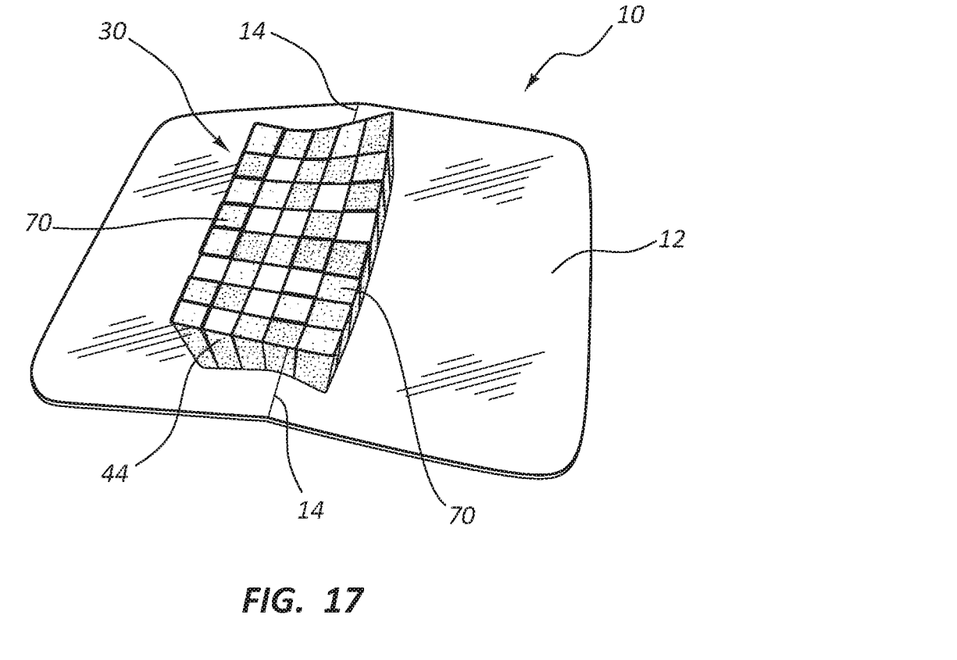
FIG. 17 is a perspective view of an application device according to one embodiment.

FIG. 17 depicts details of the applicator element 30 according to another embodiment, wherein the applicator pad 44 is attached to the outer surface of the application device package atop the partial slit 14 and defines a plurality of fingers 70. One or more incisions may be defined in the applicator pad 44 to enable the fluid 36 to migrate to the top surface of the fingers 70 after the opening 38 has been defined in the application device package. As such, the incisions are one example of one or more apertures that can be defined in the applicator element to enable fluid to migrate to a top surface of the applicator element. The fingers 70 are useful for scrubbing a surface, component, patient skin, etc. with the fluid 36. Note that, when the application device package is deformed to break the partial slit 14 and define the opening 38, the fingers 70 in one embodiment are spread apart, thus providing a multi-surface scrubbing effect. In one embodiment, the applicator pad 44 includes a closed-cell polymer foam that includes sufficient rigidity to enable scrubbing, though other materials can also be employed, including open-cell foams for instance.

Figure 18A:
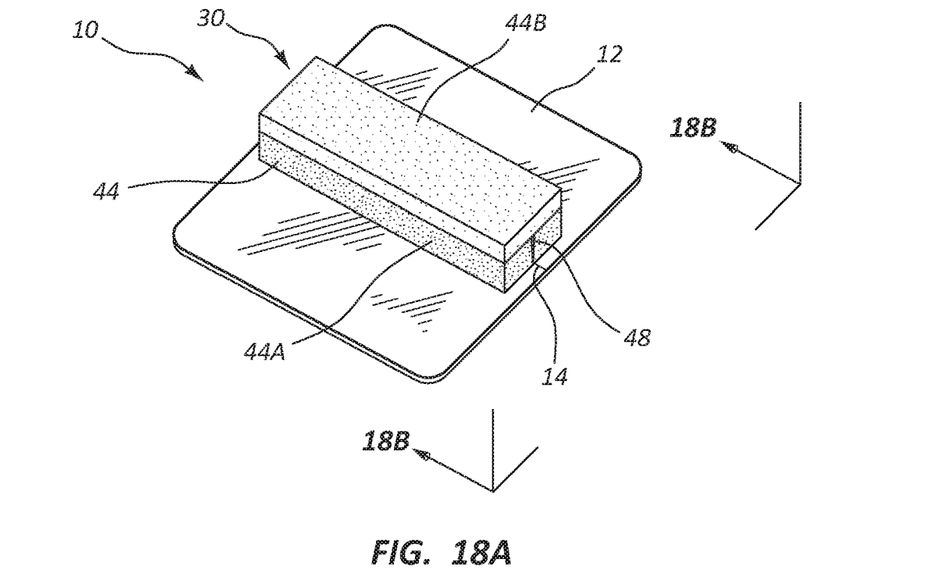
FIGS. 18A and 18B depict various views of an application device according to one embodiment.
Figure 18B:
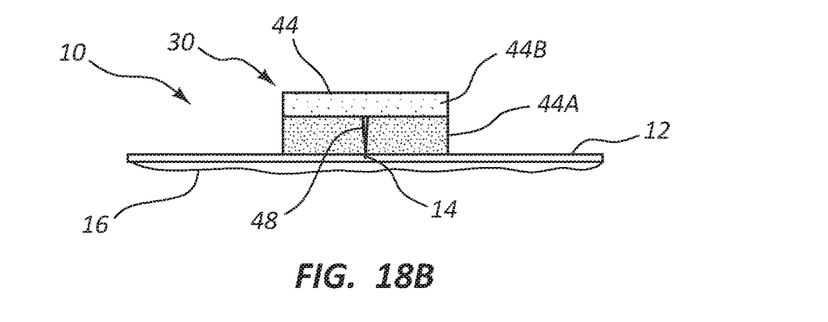

FIGS. 18A and 18B depict details of the applicator element 30 according to another embodiment, wherein the applicator pad 44 includes a base applicator pad 44A attached to the outer surface of the application device package atop the partial slit 14 and a top applicator pad 44B disposed atop the base applicator pad. The base applicator pad 44A includes a substantially non-wetting closed-cell foam and defines the incision 48 that is aligned with the partial slit 14 to enable the fluid 36 to migrate from the slit when broken and through the incision to the top applicator pad 48B, which includes a wettable open-cell foam or other suitable material including a gauze, woven or non-woven material, etc. So configured, the base applicator pad 48A provides some rigidity to the applicator element 30 while the top applicator pad 48B provides a fluid dispersal surface. The incision 48 is therefore one example of one or more apertures that can be defined in the applicator element to enable fluid to migrate to a top surface of the applicator element. In one embodiment, the base applicator pad 48A includes a polyethylene closed-cell foam and the top applicator pad 48B includes a polyurethane open-cell foam.

Figure 19:
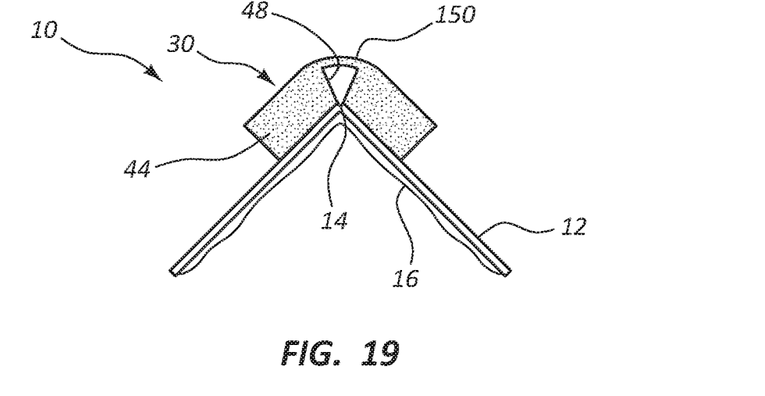
FIG. 19 is a side view of an application device according to one embodiment.

FIG. 19 depicts details of the applicator element 30 according to another embodiment, wherein the applicator pad 44 defines the incision 48 that is aligned with the partial slit 14 to enable the fluid 36 to migrate from the slit when broken and through the incision. The incision 48 does not penetrate through to the top of the applicator pad 44, thus defining a covering 150 at the top surface of the applicator pad that covers the incision. This provides a surface atop the incision 4 to assist with dispersal of the fluid. The incision 48, as before, thus serves as one example of one or more complete or partial apertures that can be defined in the applicator element to enable fluid to migrate to a top surface of the applicator element.

Note that, in one embodiment, the device 10 is included as a component in a medical kit. Further, the application device package in one embodiment can include two or more separate volumes each including a fluid, wherein the fluids can leave their respective volumes and intermix (if desired) when the package is deformed Note also that further details regarding one example of the base structure of the device package described herein can be found in U.S. Pat. No. 8,069,985 to Burattini, entitled "Sealed Single-Dose Break-Open Package," which is incorporated herein by reference in its entirety.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An application device for dispensing a fluid, comprising:
a sealed package defining a volume in which the fluid is disposed, the package including a partial slit that is configured to provide an opening to the volume when the package is deformed, wherein the package is deformed via folding the package in half such that a semi-rigid base sheet ruptures along the partial slit to provide the opening, the opening configured to enable the fluid to be released from the volume; and an applicator element initially disposed within the package, the applicator element configured to assist with dispersion of the fluid on a surface when the package is deformed so as to enable the fluid to be released from the volume; wherein the applicator element is attached to a portion of an inner surface of the semi-rigid base sheet.

2. The application device as defined in claim 1, wherein the applicator element is positioned proximate to the fluid when the fluid is released from the volume.

3. The application device as defined in claim 1, wherein the package includes the semi-rigid base sheet sealed to the cover sheet about a perimeter to define the volume.

4. The application device as defined in claim 3, wherein the cover sheet includes a foil layer.

5. The application device as defined in claim 4, wherein the semi-rigid base sheet further includes a foil layer, the foil layer of the semi-rigid base sheet and the cover sheet comprising metallic foil configured to prevent passage of ethylene oxide into the volume.

6. The application device as defined in claim 1, wherein the applicator element includes a gauze material disposed within the volume, wherein at least a portion of the gauze material is exposed at the opening when the package is deformed.

7. The application device as defined in claim 1, wherein the applicator element includes a cushioned tip that is exposed at the opening when the package is deformed.

8. The application device as defined in claim 7, wherein the cushioned tip is disposed on a rod, the rod being attached to an inner surface of one of the semi-rigid base sheet and the cover sheet.

9. The application device as defined in claim 1, wherein the applicator element is water-absorbable.

10. The application device as defined in claim 1, wherein the applicator element includes at least one of a cotton pad, a polymeric pad, a foam material, and a sponge material.

11. The application device as defined in claim 1, wherein the fluid includes a topical fluid.

12. The application device as defined in claim 1, wherein the fluid is employed in a medical application.

13. The application device as defined in claim 1, wherein the opening includes one of a linear shape, a rounded shape, and a triangular shape.

14. The application device as defined in claim 1, further comprising finger tabs included on the package to enable grasping of the package by a user.

15. The application device as defined in claim 14, wherein the finger tabs include surface features to assist with user grasping of the package.

16. The application device as defined in claim 1, wherein a shape of the package defines one of a square, rectangle, circle, hourglass, oval, and triangle.

17. The application device as defined in claim 1, further comprising a reinforcement element positioned within the volume and configured to assist with establishing the opening when the package is deformed, the reinforcement element being attached to an inner surface of one of the semi-rigid base sheet and the cover sheet of the package.

18. The application device as defined in claim 1, wherein the package is colored to indicate a type of fluid disposed therein.

* * * * *